United States Patent
Lee et al.

(10) Patent No.: US 11,192,088 B2
(45) Date of Patent: Dec. 7, 2021

(54) SUPERABSORBENT POLYMER AND METHOD FOR PREPARING THE SAME

(71) Applicant: LG Chem, Ltd., Seoul (KR)

(72) Inventors: Kum Hyoung Lee, Daejeon (KR); Gi Cheul Kim, Daejeon (KR); Sung Soo Park, Daejeon (KR); Ye Sol Yang, Daejeon (KR)

(73) Assignee: LG Chem, Ltd.

( * ) Notice: Subject to any disclaimer, the term of this patent is extended or adjusted under 35 U.S.C. 154(b) by 995 days.

(21) Appl. No.: 15/557,607

(22) PCT Filed: Apr. 14, 2016

(86) PCT No.: PCT/KR2016/003888
§ 371 (c)(1),
(2) Date: Sep. 12, 2017

(87) PCT Pub. No.: WO2017/111210
PCT Pub. Date: Jun. 29, 2017

(65) Prior Publication Data
US 2018/0043332 A1    Feb. 15, 2018

Related U.S. Application Data

(63) Continuation of application No. PCT/KR2016/003888, filed on Apr. 14, 2016.

(30) Foreign Application Priority Data

Dec. 23, 2015 (KR) .................. 10-2015-0184616
Apr. 11, 2016 (KR) .................. 10-2016-0044324

(51) Int. Cl.
| | |
|---|---|
| B01J 20/26 | (2006.01) |
| B01J 20/30 | (2006.01) |
| C08J 3/24 | (2006.01) |
| C08J 3/075 | (2006.01) |
| C08J 3/12 | (2006.01) |
| B01J 20/28 | (2006.01) |
| C08K 3/36 | (2006.01) |
| C08F 20/06 | (2006.01) |
| C08K 7/00 | (2006.01) |
| C08K 7/26 | (2006.01) |
| C08F 2/10 | (2006.01) |
| A61L 15/60 | (2006.01) |
| C08K 3/34 | (2006.01) |
| C08F 220/38 | (2006.01) |

(52) U.S. Cl.
CPC .......... B01J 20/267 (2013.01); A61L 15/60 (2013.01); B01J 20/28007 (2013.01); B01J 20/28085 (2013.01); B01J 20/3021 (2013.01); C08F 2/10 (2013.01); C08F 20/06 (2013.01); C08J 3/075 (2013.01); C08J 3/12 (2013.01); C08J 3/24 (2013.01); C08K 3/34 (2013.01); C08K 3/36 (2013.01); C08K 7/00 (2013.01); C08K 7/26 (2013.01); C08F 220/385 (2020.02); C08J 2333/02 (2013.01); C08K 2201/003 (2013.01); C08K 2201/005 (2013.01)

(58) Field of Classification Search
CPC ................ B01J 20/267; B01J 20/28007; B01J 20/28085

See application file for complete search history.

(56) References Cited

U.S. PATENT DOCUMENTS

| | | | |
|---|---|---|---|
| 4,446,261 A | 5/1984 | Yamasaki et al. | |
| 5,563,218 A | 10/1996 | Rebre et al. | |
| 5,900,437 A | 5/1999 | Mitchell et al. | |
| 5,985,944 A | 11/1999 | Ishizaki et al. | |
| 6,610,780 B1 | 8/2003 | Payzant et al. | |
| 6,750,262 B1 | 6/2004 | Hahnle et al. | |
| 2010/0100066 A1* | 4/2010 | Azad ................. | A61L 15/18 604/372 |
| 2010/0210746 A1 | 8/2010 | Gustafson et al. | |
| 2015/0210825 A1 | 7/2015 | Sadana et al. | |
| 2015/0283284 A1 | 10/2015 | Azad et al. | |
| 2016/0096944 A1* | 4/2016 | Wattebled ............. | C08L 33/02 521/123 |

FOREIGN PATENT DOCUMENTS

| | | |
|---|---|---|
| CN | 1140458 A | 1/1997 |
| CN | 1760261 A | 4/2006 |
| EP | 0615736 A1 | 9/1994 |
| EP | 0644211 A1 | 3/1995 |
| EP | 1637105 A1 | 3/2006 |
| EP | 1730218 B1 | 12/2010 |
| EP | 2797566 B1 | 6/2019 |
| JP | S56161408 A | 12/1981 |
| JP | S57158209 A | 9/1982 |
| JP | S57198714 A | 12/1982 |
| JP | 2007314794 A | 12/2007 |

(Continued)

OTHER PUBLICATIONS

Qi et al., Polym. Adv. Technol., (2010), 21, p. 196-204. (Disclosed in IDS).*

(Continued)

Primary Examiner — Yong L Chu
(74) Attorney, Agent, or Firm — Lerner, David, Littenberg, Krumholz & Mentlik, LLP

(57) ABSTRACT

The present invention relates to superabsorbent polymer having an improved absorption speed through micropores formed inside, and a method for preparing the same.

14 Claims, 2 Drawing Sheets

(56) References Cited

FOREIGN PATENT DOCUMENTS

| JP | 2009280668 A | 12/2009 | | |
|---|---|---|---|---|
| JP | 2013049868 A | 3/2013 | | |
| KR | 20130018350 A | 2/2013 | | |
| KR | 101537565 B1 | 7/2015 | | |
| KR | 20150116418 A | 10/2015 | | |
| WO | 2014183987 A1 | 11/2014 | | |
| WO | WO-2014183987 A1 * | 11/2014 | .............. | C08L 33/02 |

OTHER PUBLICATIONS

Qi, Xiaohua, "Study on the Synthesis and Swelling Kinetics of Salt-Resistant Superabsorbent Polymers", Chinese Doctoral Dissertations Full-Text Database Engineering Science & Technology I, Dec. 2009. [Partial English Translation].

Extended European Search Report for Application No. 16879078.0 dated Jul. 31, 2018, 9 pages.

Kourosh Kabiri et al., "Porous Superabsorbent Hydrogel Composites: Synthesis, Morphology and Swelling Rate", Macromolecular Materials and Engineering, vol. 289, No. 7, Jul. 14, 2004, pp. 653-661, XP055363870.

Xiaohua Qi et al., "Preparation and properties of macroporous superabsorbent composite", Polymers for Advanced Technologies, vol. 21, No. 3, Mar. 30, 2009, pp. 196-204, XP055494880.

Buchholz, et al., Modern Superabsorbent Polymer Technology, 1998, vol. 152, pp. 199-201, New York: Wiley-vch.

Third Party Observation for EP16879078.0 dated Jan. 3, 2020, 4 pages.

International Search Report for Application No. PCT/KR2016/003888 dated Jul. 29, 2016.

Odian, George, Principles of Polymerization, Wiley 1981, Second Edition, p. 203.

Schwalm, Reinhold, UV Coatings Basics, Recent Developments and New Applications, Elsevier Science 2007, p. 115.

* cited by examiner

SUPERABSORBENT POLYMER AND METHOD FOR PREPARING THE SAME

CROSS-REFERENCE TO RELATED APPLICATION

This application is a national phase entry under 35 U.S.C. § 371 of International Application No. PCT/KR2016/003888, filed Apr. 14, 2016, which claims the benefit of Korean Patent Application No. 10-2015-0184616 filed on Dec. 23, 2015, and Korean Patent Application No. 10-2016-0044324, filed on Apr. 11, 2016, with the Korean Intellectual Property Office, the disclosures of which are herein incorporated by reference in their entirety.

TECHNICAL FIELD OF THE INVENTION

The present invention relates to a superabsorbent polymer and a method for preparing the same.

More specifically, the present invention relates to a superabsorbent polymer having an improved absorption speed through micropores formed inside, and a method for preparing the same.

BACKGROUND OF THE INVENTION

A superabsorbent polymer (SAP) is a synthetic polymer material that can absorb moisture of 500 to 1000 times of self-weight, and is also named as a super absorbency material (SAM), an absorbent gel material (AGM), and so on. The superabsorbent polymer began to be commercialized as sanitary items, and currently, it is being widely used as hygienic goods such as a disposable diaper and so on, water-holding material for soil, water stop material for civil engineering and architecture, sheets for raising seedling, freshness preservatives in the field of food circulation, and so on.

As a method for preparing the superabsorbent polymer, a reverse phase suspension polymerization method or an aqueous polymerization method, and the like are known. The reverse phase suspension polymerization method is disclosed in, for example, Japanese Patent Laid-Open Publication No. Sho 56-161408, Japanese Patent Laid-Open Publication No. Sho 57-158209, and Japanese Patent Laid-Open Publication No. Sho 57-198714, and so on. And, as the aqueous polymerization method, a thermal polymerization method wherein hydrogel polymer is polymerized while breaking and cooling in a kneader equipped with several shafts, and a photopolymerization method wherein an aqueous solution of high concentration is simultaneously polymerized and dried by irradiating UV on a belt, and the like are known.

Meanwhile, an absorption speed, which is one of important properties of a superabsorbent polymer, is related to surface dryness of a product contacting skin such as a diaper. In general, such an absorption speed can be improved by widening the surface area of superabsorbent polymer.

For example, a method of forming a porous structure on the surface of superabsorbent polymer using a blowing agent is being applied. However, a sufficient amount of porous structure cannot be formed by common blowing agents, and thus, this method has a disadvantage in that increase in the absorption speed is not significant.

For another example, a method of reassembling fine particles obtained in the preparation process of superabsorbent polymer to form porous particles of irregular shapes, thereby widening the surface area, is being used. However, although the absorption speed of superabsorbent polymer may be improved through this method, the centrifuge retention capacity (CRC) and absorption under pressure (AUP) of the polymer are relatively lowered. Thus, there is an urgent demand for a preparation method capable of simultaneously improving the properties of superabsorbent polymer that are in trade-off relationship, such as absorption speed, centrifuge retention capacity, absorption under pressure, etc.

(Patent Document 1) 1. Japanese Patent Laid-Open Publication No. Sho 56-161408

(Patent Document 2) 2. Japanese Patent Laid-Open Publication No. Sho 57-158209

(Patent Document 3) 3. Japanese Patent Laid-Open Publication No. Sho 57-198714

SUMMARY OF THE INVENTION

It is an object of the present invention to provide a superabsorbent polymer having an improved absorption speed through micropores formed inside.

It is another object of the present invention to provide a method for preparing the superabsorbent polymer.

DETAILED DESCRIPTION OF THE INVENTION

Figure 1:
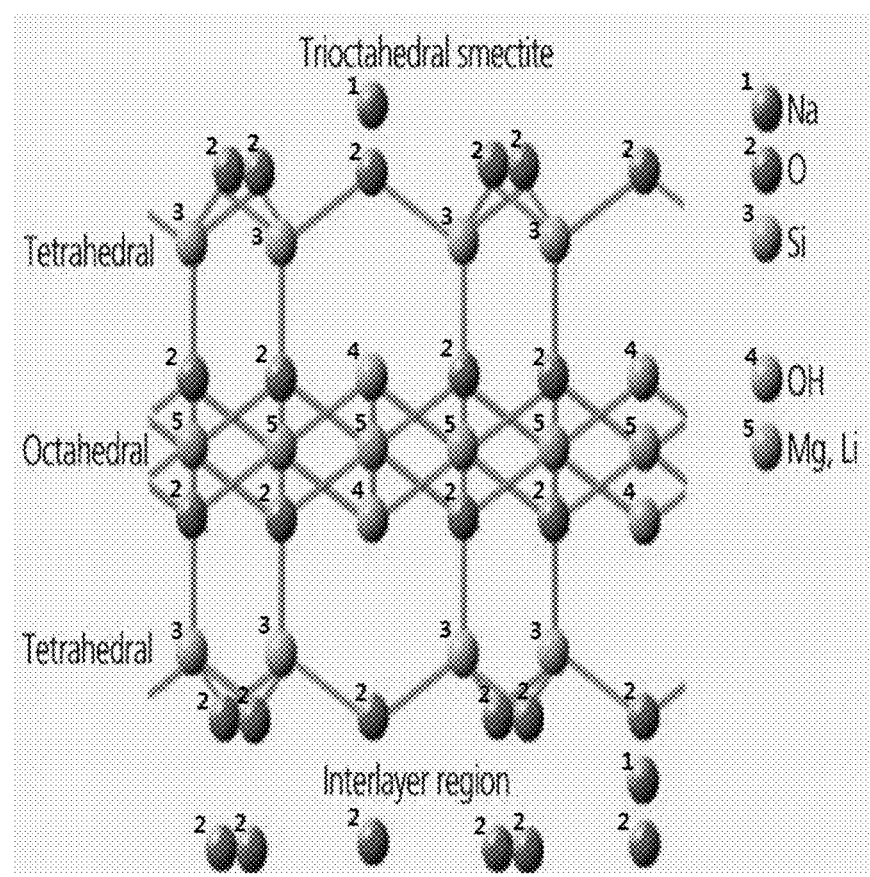
FIG. 1 schematically shows the structure of the unit crystal of the layered silicate-based particles used in Examples.

A superabsorbent polymer comprising base resin powder comprising crosslinked polymer of water soluble ethylenically unsaturated monomers having acid groups of which at least a part are neutralized, wherein a plurality of pores with a diameter of 1 µm or more are formed in the base resin powder, the crosslinked polymer comprises layered silicate-based particles dispersed in the crosslinked structure, and a time for removing vortex generated when stirring at 600 rpm in 50 ml of a 0.9 wt % NaCl solution is 60 seconds or less, is provided herein.

A method for preparing a superabsorbent polymer comprising the steps of: conducting the crosslinking polymerization of water soluble ethylenically unsaturated monomers having acid groups of which at least a part are neutralized, in the presence of layered silicate-based particles, a blowing agent and an internal crosslinking agent, to form hydrogel polymer; and drying, grinding and sieving the hydrogel polymer to form base resin powder, is also provided herein.

Hereinafter, a superabsorbent polymer and a method for preparing the same according to specific embodiments of the invention will be explained in detail.

Unless specifically described throughout the specification, "comprising" or "containing" refers to the inclusion of a certain constructional element (or constructional component) without specific limitations, and it cannot be interpreted as excluding the addition of other constructional elements (or constructional components).

As used herein, (meth)acrylate include both acrylate and methacrylate.

According to one embodiment of the present invention, a superabsorbent polymer comprising a base resin powder comprising crosslinked polymer of water soluble ethylenically unsaturated monomers having acid groups of which at least a part are neutralized, wherein a plurality of pores with a diameter of 1 μm or more are formed in the base resin powder, the crosslinked polymer comprises layered silicate-based particles dispersed in the crosslinked structure, and a time for removing vortex generated when stirring at 600 rpm in 50 ml of a 0.9 wt % NaCl solution is 60 seconds or less, is provided.

The present inventors confirmed through the experiments that if using the above explained superabsorbent polymer, since specific layered silicate-based particles are used, a plurality of micropores can be stably formed in the crosslinked polymer, and thus, the contact area with water may rapidly increase and the absorption speed of the superabsorbent polymer may be further improved, and completed the present invention.

Specifically, the superabsorbent polymer may comprise a base resin powder comprising crosslinked polymer of water soluble ethylenically unsaturated monomers having acid groups of which at least a part are neutralized. The "crosslinked polymer of water soluble ethylenically unsaturated monomers" includes a hydrogel polymer formed immediately after progressing the thermal polymerization or photopolymerization of a composition containing water soluble ethylenically unsaturated monomers, a polymer obtained by drying the hydrogel polymer according to a common preparation method of a superabsorbent polymer, a polymer obtained by grinding the hydrogel polymer or dried polymer, a polymer before conducting a surface crosslinking reaction, or a polymer after conducting a surface crosslinking reaction, etc., and any polymer may be included regardless of the shape, moisture content, particle diameter, whether or not surface crosslinked, etc., as long as it is formed by the polymerization of water soluble ethylenically unsaturated monomers.

The superabsorbent polymer of one embodiment basically comprises crosslinked polymer of water soluble ethylenically unsaturated monomers as base resin powder, similarly to the previous superabsorbent polymer.

In the superabsorbent polymer of one embodiment, as the water soluble ethylenically unsaturated monomers, one or more kinds selected from the group consisting of anionic monomers and salts thereof such as acrylic acid, methacrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid or 2-(meth)acrylamide-2-methyl propane sulfonic acid; non-ionic hydrophilic group containing monomers such as (meth)acrylamide, N-substituted (meth)acrylate, 2-hydroxyethyl (meth)acrylate, 2-hydroxypropyl (meth)acrylate, methoxy polyethylene glycol (meth)acrylate, or polyethylene glycol (meth)acrylate; and amino group containing unsaturated monomers such as (N,N)-dimethylaminoethyl (meth)acrylate, (N,N)-dimethylaminopropyl (meth)acrylamide, and quarternarized products thereof, may be used. Among them, acrylic acid or salts thereof, for example, acrylic acid and/or alkali metal salts such as a sodium salt thereof, in which at least a part of the acrylic acid is neutralized, may be used, and by using such monomers, a superabsorbent polymer having more excellent properties can be prepared. In case the alkali metal salt of acrylic acid is used as monomers, the acrylic acid may be neutralized with a basic compound such as caustic soda (NaOH) before use.

And, the crosslinked polymer included in the base resin powder may comprise a crosslinking structure in which the polymer chains of the water soluble ethylenically unsaturated monomers are crosslinked through the crosslinkable functional group of an internal crosslinking agent. As the internal crosslinking agent for introducing a basic crosslinking structure into the crosslinked polymer and baser resin powder, all internal crosslinking agents having crosslinkable functional groups previous used in the preparation of superabsorbent polymer may be used without specific limitations. However, in order to introduce an appropriate crosslinking structure into the crosslinked polymer and baser resin powder and further improve the properties of superabsorbent polymer, a multifunctional acrylate-based compound having a plurality of ethylene oxide groups may be used as the internal crosslinking agent. Specific examples of the internal crosslinking agent may include one or more selected from the group consisting of polyethyleneglycol diacrylate (PEGDA), glycerin diacrylate, glycerin triacrylate, non-modified or ethoxlyated trimethylol propane triacrylate (TMPTA), hexanedioldiacrylate, and triethyleneglycol diacrylate.

Figure 2:
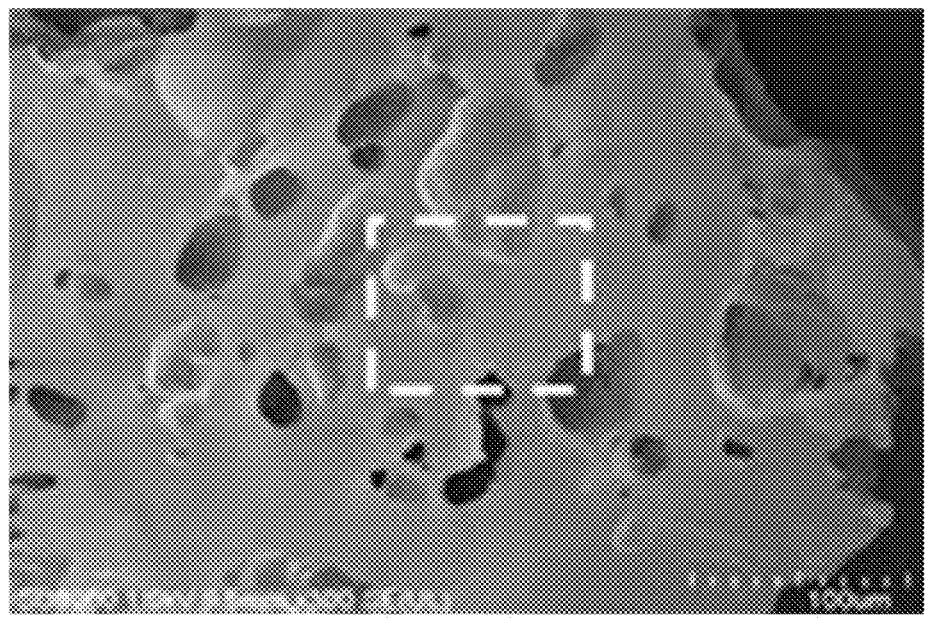
FIG. 2 is the surface SEM image of the superabsorbent polymer prepared in Examples.

Meanwhile, a plurality of pores with a diameter of 1 μm or more may be formed in the base resin powder. The pores are realized by a blowing agent added together in the monomer composition, as shown in the preparation method of superabsorbent polymer described below, and it can be confirmed that a plurality of pores with the minimum diameter of 1 μm or more are formed in the base resin powder, as shown in FIG. 2. The pores may exist while being uniformly dispersed inside the base resin powder, singularly or plurally.

Particularly, among the pores with a diameter of 1 μm or more included in the base rein powder, micropores with diameter of 10 μm to 100 μm may be included. The micropores with diameter of 10 μm to 100 μm may be formed by adding a blowing agent and inorganic particles together when forming polymer, as explained below, and since such micropores are stably formed, the contact area with water may be increased, thus further improving the absorption speed of superabsorbent polymer.

And, the crosslinked polymer included in the base resin powder may comprise layered silicate-based particles dispersed in the crosslinking structure. As the layered silicate-based particles, particles comprising a unit crystal comprising a metal oxide layer, and a silica layer comprising silica formed on at least one side of the metal oxide layer, may be used.

The unit crystal means a periodic unit of a crystalline particle having three-dimensional periodicity, and particles may be formed through the repetition of the unit crystals.

The unit crystal of the layered silicate-based particle may comprise a unit crystal comprising a metal oxide layer, and a silica layer comprising silica formed on at least one side of the metal oxide layer. That is, in the unit crystal of the layered silicate-based particle, a silica layer may be formed on one side or both sides of the metal oxide layer.

Specifically, the metal oxide layer and the silica layer may be bonded through a siloxane bond. The siloxane bond means a covalent bond between a silicon atom (Si) and an oxygen atom (O), and more specifically, as in the unit crystal structure shown in FIG. 1, the bond between the metal oxide layer and the silica layer may be formed through the covalent bond between oxygen atoms included in an octahedral metal oxide layer and silicon atoms included in a tetrahedral silica layer.

In the metal oxide layer, the metal oxide may exist while metal atoms and oxygen atoms are bonded, and the examples of the metal atom are not specifically limited, and may include atoms in Group 1 or 2 of the periodic table, i.e., lithium, sodium, potassium, beryllium, magnesium calcium, etc.

Thus, the layered silicate-based particles may stably maintain micropores in the crosslinked polymer, to increase the contact area with water, thereby further improving the absorption speed of superabsorbent polymer.

The layered silicate-based particles may have a column structure with the maximum diameter of the vertical cross section of 1 nm to 100 nm, and the height of 0.1 nm to 20 nm. The column structure means a solid figure wherein the upper and the lower sides are parallel to each other. Specific shapes of the column structure are not limited, but, for example, may include a cylinder, an elliptic cylinder, a polyprism, etc. according to the kind of the cross section formed by cutting the layered silicate-based particle in a direction parallel to the ground, i.e., the kind of the figure exhibited by the vertical cross section.

As explained above, the column structure of the layered silicate-based particle may be formed through the repetition of the unit crystals, and in the column structure, the maximum diameter of the vertical cross section means the largest value among the diameters of the cross sections formed by cutting the layered silicate-based particle in a direction parallel to the ground.

As such, since the layered silicate-based particle has a column structure with the maximum diameter of the vertical cross section of 1 nm to 100 nm, and the height of 0.1 nm to 20 nm, the layered silicate-based particles may not only realize the functionality in the cross linked polymer through the fine particle size, but also stabilize micropores formed by a blowing agent in a monomer composition when forming cross linked polymer.

Although examples of the layered silicate-based particles are not significantly limited, for example, they may include hectorite (Laponite RD, Laponite XLG, Laponite D, Laponite DF, Laponite RS, Laponite XLS, Laponite DS, Laponite S and Laponite JS, etc.), more preferably, Laponite RD.

And, the above explained layered silicate-based particles may be included in the content of 0.01 parts by weight to 5 parts by weight, based on 100 parts by weight of the base resin powder. Thereby, the degree of formation of micropores in the cross linked polymer may be optimized, and thus, the superabsorbent polymer of one embodiment may have more improved absorption speed.

Specifically, the superabsorbent polymer of one embodiment may have a time for removing vortex generated when stirring at 600 rpm in 50 ml of a 0.9 wt % NaCl solution, of 60 seconds or less, or 40 to 60 seconds, or 50 to 58 seconds. When stirring at 600 rpm in 50 ml of a 0.9 wt % NaCl solution, the superabsorbent polymer of one embodiment is added in the 0.9 wt % NaCl solution and stirred, and vortex may be removed by the absorption capacity of the superabsorbent polymer.

More specifically, the time for removing vortex may be calculated by adding 2.00 g of the superabsorbent polymer of one embodiment while stirring in 50 ml of a 0.9 wt % NaCl solution at 600 rpm using a stirrer, and measuring a time until the vortex of liquid generated by the stirring disappears and a smooth surface is formed.

If the time for removing vortex generated when stirring at 600 rpm in 50 ml of a 0.9 wt % NaCl solution increases to greater than 60 seconds, the absorption speed of the superabsorbent polymer may become slow, and thus, it may be difficult to realize a prompt absorption capacity when applied to a product such a diaper. In the prior art, there was only an attempt to apply a blowing agent to increase the surface area through the porous structure so as to improve the absorption speed of superabsorbent polymer, while in the present invention, by adding specific inorganic particles together with a blowing agent, remarkably improved absorption speed compared to the prior art can be realized.

And, the superabsorbent polymer may have a centrifuge retention capacity for a saline solution, measured according to EDANA method WSP 241.2, of 45 g/g or more, or 45 g/g to 60 g/g. The centrifuge retention capacity (CRC) for a saline solution may be measured according to EDANA method WSP 241.2. More specifically, the centrifuge retention capacity may be calculated by the following Equation 1, after absorbing superabsorbent polymer in a saline solution over 30 minutes.

$$CRC(g/g) = \{[W_2(g) - W_1(g)]/W_0(g)\} - 1 \quad \text{[Equation 1]}$$

In the Equation 1, $W_0(g)$ is the initial weight of superabsorbent polymer, $W_1(g)$ is the weight of an apparatus measured after dehydrating at 250 G for 3 minutes using a centrifuge, and $W_2(g)$ is the weight of an apparatus including a superabsorbent polymer measured after immersing a superabsorbent polymer in a 0.9 wt % saline solution for 30 minutes to absorb, and then, dehydrating at 250 G for 3 minutes using a centrifuge.

And, the superabsorbent polymer of one embodiment may have a particle morphology such as a globular shape with a particle diameter of about 150 μm to 850 μm or amorphous shape, etc.

Meanwhile, according to another embodiment of the invention, a method for preparing a superabsorbent polymer comprising the steps of: conducting the crosslinking polymerization of water soluble ethylenically unsaturated monomers having acid groups of which at least a part are neutralized, in the presence of layered silicate-based particles, a blowing agent and an internal crosslinking agent, to form hydrogel polymer; and drying, grinding and sieving the hydrogel polymer to form base resin powder, is provided.

In the preparation method of another embodiment, the layered silicate-based particles are used together with common blowing agent and internal cross linking agent, to progress the crosslinking polymerization of water soluble ethylenically unsaturated monomers, followed by drying, grinding, sieving and surface crosslinking, etc. according to a common preparation method of a superabsorbent polymer, thus preparing a superabsorbent polymer. As such, in the step of crosslinking polymerization of water soluble ethylenically unsaturated monomers, by using the layered silicate-based particles together with a blowing agent, micropores generated by the blowing agent may be stably maintained by the layered silicate-based particles, and thus, the absorption speed of the finally prepared superabsorbent polymer may be further improved, and base resin powder into which a cross linking structure already formed by the use of an internal cross linking agent is introduced can be prepared, thereby realizing excellent properties such as centrifuge retention capacity, etc.

By the preparation method of a superabsorbent polymer of another embodiment, the superabsorbent polymer of one embodiment can be prepared.

Specifically, the preparation method of superabsorbent polymer may comprise the step of progressing the cross linking polymerization of water soluble ethylenically unsaturated monomers having acid groups of which at least a part are neutralized, in the presence of layered silicate-based particles, a blowing agent and an internal crosslinking agent, to form hydrogel polymer.

As the layered silicate-based particles, particles comprising unit crystals comprising a metal oxide layer comprising metal oxide, and a silica layer comprising silica, formed on at least one side of the metal oxide layer, may be used.

The unit crystal means a periodic unit of a crystalline particle having three-dimensional periodicity, and particles may be formed through the repetition of the unit crystals.

The unit crystal of the layered silicate-based particle may comprise a metal oxide layer comprising metal oxide, and a silica layer comprising silica, formed on at least one side of the metal oxide layer. That is, in the unit crystal of the layered silicate-based particle, a silica layer may be formed on one side or both sides of the metal oxide layer.

Specifically, the metal oxide layer and the silica layer may be bonded through a siloxane bond. The siloxane bond means a covalent bond between a silicon atom(Si) and an oxygen atom(O), and more specifically, as in the unit crystal structure shown in FIG. 1, the bond between the metal oxide layer and the silica layer may be formed through the covalent bond between oxygen atoms included in an octahedral metal oxide layer and silicon atoms included in a tetrahedral silica layer.

In the metal oxide layer, the metal oxide may exist while metal atoms and oxygen atoms are bonded, and the examples of the metal atom are not specifically limited, and may include atoms in Group 1 or 2 of the periodic table, i.e., lithium, sodium, potassium, beryllium, magnesium calcium, etc.

The layered silicate-based particles may have a column structure with the maximum diameter of the vertical cross section of 1 nm to 100 nm, and height of 0.1 nm to 20 nm. The column structure means a solid figure wherein the upper and the lower sides are parallel to each other. Specific shapes of the column structure are not limited, but, for example, may include a cylinder, an elliptic cylinder, a polyprism, etc. according to the kind of the cross section formed by cutting the layered silicate-based particle in a direction parallel to the ground, i.e., the kind of the figure exhibited by the vertical cross section.

As explained, above, the column structure of the layered silicate-based particle may be formed through the repetition of the unit crystals, and in the column structure, the maximum diameter of the vertical cross section means the largest value among the diameters of the cross sections formed by cutting the layered silicate-based particle in a direction parallel to the ground.

As such, since the layered silicate-based particle has a column structure with the maximum diameter of the vertical cross section of 1 nm to 100 nm, and the height of 0.1 nm to 20 nm, the layered silicate-based particles may not only realize the functionality in the cross linked polymer through the fine particle size, but also stabilize micropores formed by a blowing agent in a monomer composition when forming the cross linked polymer.

Although examples of the layered silicate-based particles are not significantly limited, for example, they may include hectorite (Laponite RD, Laponite XLG, Laponite D, Laponite DF, Laponite RS, Laponite XLS, Laponite DS, Laponite S and Laponite JS, etc.), more preferably, Laponite RD.

Examples of the blowing agent are not specifically limited, and previously known various blowing agents may be used without limitations. Specifically, for example, it may include one or more selected from the group consisting of azodicarbonamide, azodicarboxylamide, benzenesulfonyhydrazide, dinitrosopentamethylenetetramine, toluenesulfonylhydrazide, azobisisobutyronitrile, barium azodicarboxylate, and sodium bicarbonate.

As explained above, the step of progressing the cross linking polymerization of water soluble ethylenically unsaturated monomers having acid groups of which at least a part are neutralized to form hydrogel polymer may be progressed in the presence of layered silicate-based particles, a blowing agent and an internal crosslinking agent.

As such, instead of forming hydrogel polymer and then adding layered silicate-based particles, a blowing agent, etc., by adding the layered silicate-based particles and blowing agent to a monomer composition for forming hydrogel polymer, micropores can be formed even inside of the hydrogel polymer.

Here, based on 100 parts by weight of the blowing agent, the content of the layered silicate-based particles may be 1 part by weight to 1000 parts by weight, or 1 part by weight to 500 parts by weight, or 1 part by weight to 100 parts by weight, or 1 part by weight to 50 parts by weight, or 10 parts by weight to 30 parts by weight. If the content of the layered silicate-based particles too decreases based on the content of the blowing agent, the pore stabilization effect by the layered silicate-based particles may decrease, and thus, the absorption capacity of the superabsorbent polymer may decrease.

On the contrary, if the content of the layered silicate-based particles too increases based on the content of the blowing agent, the viscosity of a solution in which the layered silicate-based particles are dispersed may rapidly increase, and thus, transfer of the superabsorbent polymer during the manufacturing process may become difficult.

Meanwhile, the step of forming hydrogel polymer, more specifically, may comprise the steps of: forming a first solution comprising an internal crosslinking agent, and water soluble ethylenically unsaturated monomers having acid groups of which at least a part are neutralized; forming a second solution comprising layered silicate-based particles and a blowing agent; and progressing the crosslinking polymerization of a monomer composition comprising the first solution and the second solution.

The details of the internal cross linking agent, water soluble ethylenically unsaturated monomers having acid groups of which at least a part are neutralized, layered silicate-based particles and blowing agent are as explained in one embodiment.

Specifically, in the step of forming a first solution comprising an internal crosslinking agent, and water soluble ethylenically unsaturated monomers having acid groups of which at least a part are neutralized, the content of the internal crosslinking agent may be 0.01 parts by weight to 5 parts by weight, based on 100 parts by weight of the water soluble ethylenically unsaturated monomers.

And, in the step of forming a second solution comprising layered silicate-based particles and a blowing agent, as explained above, the content of the layered silicate-based particles may be 1 part by weight to 1000 parts by weight, or 1 part by weight to 500 parts by weight, or 1 part by weight to 100 parts by weight, or 1 part by weight to 50 parts by weight, or 10 parts by weight to 30 parts by weight, based on 100 parts by weight of the blowing agent.

And, in the step of crosslinking polymerization of a monomer composition comprising the first solution and the second solution, the content of the second solution may be 1 part by weight to 100 parts by weight, or 50 parts by weight to 100 parts by weight, or 80 parts by weight to 100 parts by weight, based on 100 parts by weight of the first solution included in the monomer composition.

Each of the first solution, second solution, monomer composition may independently further comprise a polymerization initiator commonly used for the preparation of superabsorbent polymer.

Specifically, as the polymerization initiators, a thermal polymerization initiator or a photopolymerization initiator according to UV irradiation, and so on, may be used according to polymerization methods. However, even in the case of photopolymerization, since a certain amount of heat is generated by UV irradiation, etc., and heat is generated to some degree according to the progression of an exothermic polymerization reaction, a thermal polymerization initiator may be additionally included.

The photopolymerization initiator is not limited in terms of its construction, as long as it is a compound capable of forming a radical by light such as UV.

As the photopolymerization initiator, for example, one or more compounds selected from the group consisting of benzoin ether, dialkyl acetophenone, hydroxyl alkylketone, phenyl glyoxylate, Benzyl Dimethyl Ketal, acyl phosphine, and α-aminoketone may be used. As the specific example of the acyl phosphine, commercially used lucirin TPO, namely, 2,4,6-trimethyl-benzoyl-trimethyl phosphine oxide may be used. More various photopolymerization initiators are described in Reinhold Schwalm, "UV Coatings: Basics, Recent Developments and New Application (Elsevier 2007)", page 115, and are not limited to the above described examples.

The photopolymerization initiator may be added in the concentration of about 0.01 to about 1.0 wt %, based on the monomer composition. If the concentration of the photopolymerization initiator is too low, polymerization speed may become slow, and if the concentration of the polymerization initiator is too high, the molecular weight of the superabsorbent polymer may be small and the properties may become nonuniform.

And, as the thermal polymerization initiator, at least one selected from the group consisting of a persulfate initiator, an azo initiator, hydrogen peroxide, and ascorbic acid may be used. Specific examples of the persulfate initiator may include sodium persulfate ($Na_2S_2O_8$), potassium persulfate ($K_2S_2O_8$), ammonium persulfate (($NH_4)_2S_2O_8$), etc., and, specific examples of the azo initiator may include 2,2-azobis(2-amidinopropane)dihydrochloride, 2,2-azobis-(N,N-dimethylene)isobutyramidinedihydrochloride, 2-(carbamoylazo)isobutyronitril, 2,2-azobis[2-(2-imidazolin-2-yl)propane]dihydrochloride, 4,4-azobis-(4-cyanovalericacid), etc. More various thermal initiators are described in "Principle of Polymerization (Wiley, 1981)", Odian, page 203, and are not limited to the above described examples.

The thermal polymerization initiator may be included in the concentration of about 0.001 to about 0.5 wt %, based on the monomer composition. If the concentration of the thermal polymerization initiator is too low, additional thermal polymerization may hardly occur, and thus, the effect according to the addition of the thermal polymerization initiator may be insignificant, and if the concentration of the thermal polymerization initiator is too high, the molecular weight of the superabsorbent polymer may be small, and the properties may become nonuniform.

In the monomer composition comprising the first solution and the second solution, the concentration of the water soluble ethylenically unsaturated monomers may be 20 wt % to about 60 wt %, or 40 wt % to about 50 wt %, based on the total monomer composition comprising the above explained raw materials and solvents, and it may be controlled to an appropriate concentration considering the polymerization time and reaction conditions, etc. However, if the concentration of the monomers is too low, the yield of the superabsorbent polymer may be low, thus generating economical problem, and if the concentration is too high, a part of the monomers may be precipitated or grinding efficiency may be low when grinding polymerized hydrogel polymer, thus generating process problems, and the properties of the superabsorbent polymer may be deteriorated.

Each of the first solution, the second solution, and the monomer composition may independently further comprise a thickener, a plasticizer, a preservation stabilizer, an antioxidant, a neutralizing agent, etc., as necessary.

The neutralizing agent is added so as to prevent pH decrease due to the water soluble ethylenically unsaturated monomers, and is not specifically limited as long as it is basic material with pH 7 or more. Examples of the neutralizing agent may include caustic soda (NaOH), etc.

Although examples of the method of adding the neutralizing agent to the monomer composition are not specifically limited, for example, the neutralizing agent may be introduced into the first solution comprising an internal cross linking agent and water soluble ethylenically unsaturated monomers having acid group of which at least a part are neutralized, and then, the second solution comprising layered silicate-based particles and a blowing agent may be added.

The above explained raw materials such as water soluble ethylenically unsaturated monomers, silicate-based particles, photopolymerization initiator, thermal polymerization initiator, internal cross linking agent and additives may be added while being dissolved in a solvent.

Here, the solvent that can be used is not limited in terms of its construction as long as it can dissolve the above explained components, and for example, water, ethanol, ethyleneglycol, diethyleneglycol, triethyleneglycol, 1,4-butanediol, propyleneglycol, ethyleneglycol monobutyl ether, propyleneglycol monomethyl ether, propyleneglycol monomethyl ether acetate, methylethylketone, acetone, methylamylketone, cyclohexanone, cyclopentanone, diethyleneglycol monomethyl ether, diethyleneglycol ethyl ether, toluene, xylene, butyrolactone, carbitol, methylcellosolve acetate and N,N-dimethylacetamide, or a mixture thereof may be used.

Meanwhile, a method of forming hydrogel polymer by the thermal polymerization or photopolymerization of the monomer composition is not specifically limited in terms of its construction, as long as it is a commonly used polymerization method.

Specifically, the polymerization method is largely classified into thermal polymerization and photopolymerization according to energy source, and commonly, thermal polymerization may be progressed in a reactor equipped with a stirring axis such as a kneader, and photopolymerization may be progressed in a reactor equipped with a movable conveyer belt, but the above explained polymerization methods are no more than examples, and the present invention is not limited thereto.

For example, hydrogel polymer may be obtained by supplying hot wind into a reactor equipped with a stirring axis such as a kneader or heating the reactor, thereby progressing thermal polymerization, and the hydrogel polymer discharged to the outlet of the reactor may be in the form of a few centimeters to a few millimeters according to the shape of the stirring axis equipped in the reactor. Specifically, the size of obtained hydrogel polymer may vary according to the concentration of the introduced monomer composition and the introduction speed, and so on, and commonly, hydrogel polymer having a (weight average) particle diameter of 2 to 50 mm may be obtained.

And, in case photopolymerization is progressed in a reactor equipped with a movable conveyer belt as explained above, the obtained hydrogel polymer may be in the form of a sheet having the width of the belt. Here, the thickness of the polymer sheet may vary according to the concentration of the introduced monomer composition and the introduction speed, but, commonly, a monomer composition is preferably fed such that polymer in the form of a sheet having a thickness of about 0.5 cm to about 5 cm may be obtained. In case a monomer composition is fed such that the thickness of sheet-shaped polymer may be too thin, production efficiency may be low, and if the thickness of the sheet-shaped polymer is greater than 5 cm, due to the too thick thickness, a polymerization reaction may not uniformly occur throughout the whole thickness.

The hydrogel polymer obtained by such a method may exhibit a moisture content of about 40 to about 80 wt %. Here, the "moisture content" is the content of occupying moisture based on the total weight of hydrogel polymer, and it means a value obtained by subtracting the weight of polymer of a dry state from the weight of hydrogel polymer. Specifically, it is defined as a value calculated by measuring the weight loss according to moisture evaporation in the polymer while raising the temperature of polymer through infrared heating to dry. At this time, the drying condition is established such that the temperature is raised from room temperature to about 180° C. and then maintained at 180° C., and the total drying time is 20 minutes including a temperature raising step of 5 minutes.

And, after the cross linking polymerization of the monomers, base resin powder may be obtained through the processes of drying, grinding and sieving, etc., and it is preferable that the base resin powder and the superabsorbent polymer obtained therefrom is prepared and provided with a particle diameter of about 150 µm to 850 µm. More specifically, at least about 95 wt % of the base resin powder and the superabsorbent polymer obtained therefrom may have a particle diameter of about 150 µm to 850 µm, and less than about 3 wt % thereof may have a particle diameter of less than about 150 µm.

As such, since the particle diameter distribution of the base resin powder and the superabsorbent polymer is controlled to a preferable range, the finally prepared superabsorbent polymer may exhibit the above explained properties and more excellent permeability.

Meanwhile, the method of progressing drying, grinding and sieving will be explained below.

First, in the step of drying hydrogel polymer, if necessary, in order to increase the efficiency of the drying step, a step of coarse crushing may be conducted before drying. Here, grinders that can be used in the coarse crushing is not limited in terms of the constructions, but specifically, one selected from the group consisting of a vertical pulverizer, a turbo cutter, a turbo grinder, a rotary cutter mill, a cutter mill, a disc mill, a shred crusher, a hammer mill, a crusher, a chopper, a disc cutter may be used, but is not limited thereto.

The coarse crushing step may be progressed such that the particle diameter of hydrogel polymer may become about 2 mm to about 10 mm Crushing to a particle of less than 2 mm would not be technically easy due to the high moisture content of the hydrogel polymer, and may generate agglomeration between the ground particles. Meanwhile, if grinding to a particles diameter greater than 10 mm, the effect of increasing the efficiency of the subsequent drying step may be insignificant.

The hydrogel polymer coarse-crushed as explained above, or hydrogel polymer immediately after polymerization without passing the coarse-crushing step is dried. Here, the drying temperature may be about 150° C. to about 250° C. If the drying temperature is less than about 150° C., a drying time may too lengthen, and the properties of the finally prepared superabsorbent polymer may be deteriorated, and if the drying temperature is greater than about 250° C., only the surface of hydrogel polymer may be dried, thus generating a lot of fine particles in the grinding process as described below, and the properties of the finally prepared superabsorbent polymer may be degraded. Thus, the drying may be progressed at a temperature of about 150° C. to about 200° C.

Meanwhile, the drying may be progressed for about 20 minutes to about 90 minutes considering the process efficiency, etc., but the drying time is not limited thereto.

And, the drying method is not limited in terms of the construction as long as it can be commonly used as a drying process of hydrogel polymer. Specifically, in the drying step, hot wind supply, infrared ray irradiation, ultrahigh frequency wave irradiation, or UV irradiation, etc., may be applied. The polymer dried by such a method may exhibit a moisture content of about 0.1 to 10 wt %.

Next, a step of grinding the dried polymer obtained through the drying step is progressed.

The particle diameter of the polymer powder obtained after grinding may be about 150 µm to about 850 µm. As a grinder for grinding to such a particle diameter, specifically, a pin mill, a hammer mill, a screw mill, a roll mill, a disc mill, a jog mill, or a sieve, etc. may be used, but the grinder is not limited thereto.

And, in order to manage the properties of the finally productized superabsorbent polymer after the grinding step, a step of sieving the polymer powder obtained after grinding according to the particle diameter may be conducted. Preferably, polymer with a particle diameter of about 150 µm to about 850 µm may be sieved, and only the polymer powder having such particle diameters may be additionally passed through the step of surface cross linking reaction, etc., as necessary, to productize it. The particle diameter distribution of the base resin powder obtained through these processes has been already explained, and the detailed explanations are omitted.

According to the present invention, a superabsorbent polymer having an improved absorption speed through micropores formed inside, and a method for preparing the same are provided.

Hereinafter, the present disclosure will be explained in detail with reference to the following examples. However, these examples are only to illustrate the inventive concept, and the scope of the inventive concept is not limited thereto.

Examples 1 to 2: Preparation of Superabsorbent Polymer

Example 1

Into 226 g of acrylic acid, 0.18 g of bis(2,4,6-trimethyl-benzoyl)-phenyl phosphine oxide (IGARCURE 819) was introduced as a photopolymerization initiator, and mixed for 5 minutes, and then, 5.2 g of polyethyleneglycol diacrylate (Miramer M280) was introduced as a cross linking agent, and mixed for 10 minutes, thus preparing a monomer solution.

Into 156 g of ionized water, 3.5 g of sodium persulfate was introduced as a thermal polymerization initiator, and completely dissolved in the ionized water, and then, 3.2 g of layered silicate-based particles laponite RD were introduced as inorganic particles, and mixed for 30 minutes. Thereafter, 17.7 g of sodium bicarbonate was introduced as a blowing agent, and mixed for 10 minutes, thus preparing a mixed aqueous solution.

661 g of 32% caustic soda (NaOH) was mixed with 195 g of ionized water to prepare a caustic soda solution.

Into a 2 L dual jacketed glass reactor in which 20° C. cooling water flows, 483 g of acrylic acid was introduced, and 55 g of the monomer solution was introduced and mixed for 5 minutes. Thereafter, the caustic soda solution was introduced for 10 minutes to neutralize. The temperature increased to about 65° C. by the neutralization heat, and after waiting until the solution was cooled to 42° C., 54.8 g of the mixed aqueous solution was introduced and mixed for 1 minute, thus preparing a monomer composition.

The monomer composition was introduced into a feeder of a polymerization reactor consisting of continuously moving conveyer belt, irradiated by UV for 1 minute using a UV irradiation device with the illumination of 10 mW (irradiation amount: 2 mW/cm$^2$), and after waiting for 2 minutes, cut to a size of 5 cm*5 cm, and then, ionized water was introduced and absorbed, thus obtaining hydrogel polymer.

The hydrogel polymer was transferred to a cutter, and then, crushed at 25° C., 15.8 hz. Subsequently, the crushed hydrogel polymer was dried in a hot air dryer of 180° C. for 40 minutes, and the dried hydrogel polymer was ground with a hammer mill grinder. Subsequently, using a sieve, polymer having a particle diameter (average particle diameter) of 150 μm to 850 μm was sieved, and polymer having a particle diameter (average particle diameter) of 300 μm to 600 μm was sieved to prepare a superabsorbent polymer.

Example 2

A superabsorbent polymer was prepared by the same method as Example 1, except that 3.4 g of polyethylenediacrylate (Mw=280) was added as a cross linking agent when preparing the mixed aqueous solution.

Comparative Examples 1 to 3: Preparation of Superabsorbent Polymer

Comparative Example 1

A superabsorbent polymer was prepared by the same method as Example 1, except that 3.2 g of laponite RD and 17.7 g of sodium bicarnonate were not added when preparing the monomer solution.

Comparative Example 2

A superabsorbent polymer was prepared by the same method as Example 1, except that 17.7 g of sodium bicarnonate was not added when preparing the monomer solution.

Comparative Example 3

Into 200 g of acrylic acid, 0.43 g of bis(2,4,6-trimethylbenzoyl)-phenyl phosphine oxide (IGARCURE 819) was introduced as a photopolymerization initiator, and mixed for 5 minutes, thus preparing a photoinitiator solution.

Into 164.5 g of acrylic acid, 5.2 g of polyethyleneglycoldiacrylate (Mw=508) [Miramer M280] was introduced as a cross linking agent and mixed for 5 minutes, thus preparing a cross linking agent solution.

Into 96.7 g of ionized water, 10.7 g of sodium persulfate was introduced as a thermal polymerization initiator, and completely dissolved in the ionized water, thus preparing an initiator solution.

Into 76.7 g of ionized water, 1.6 g of sodium bicarbonate was introduced as a blowing agent, and completely dissolved in the ionized water, thus preparing a blowing agent solution.

653 g of 32% caustic soda (NaOH) was mixed with 120 g of ionized water to prepare a caustic soda solution.

Into a 2 L dual jacketed glass reactor in which 20° C. cooling water flows, 501 g of acrylic acid was introduced, and 20 g of the photoinitiator solution and 18.3 g of the cross linking agent solution were introduced and mixed for 5 minutes. Thereafter, the caustic soda solution was introduced for 10 minutes to neutralize. The temperature increased to about 65° C. by the neutralization heat, and after waiting until the solution was cooled to 42° C., 10.8 g of the thermal initiator solution and 78.3 g of the blowing agent solution were mixed for 1 minute to prepare a monomer composition.

The monomer composition was introduced into a feeder of a polymerization reactor consisting of continuously moving conveyer belt, irradiated by UV for 1 minute using a UV irradiation device with the illumination of 10 mW (irradiation amount: 2 mW/cm$^2$), and after waiting for 2 minutes, cut to a size of 5 cm*5 cm, and then, ionized water was introduced and absorbed, thus obtaining hydrogel polymer.

The hydrogel polymer was transferred to a cutter, and then, crushed at 25° C., 15.8 hz. Subsequently, the crushed hydrogel polymer was dried in a hot air dryer of 180° C. for 40 minutes, and the dried hydrogel polymer was ground with a hammer mill grinder. Subsequently, using a sieve, polymer having a particle diameter (average particle diameter) of 150 μm to 850 μm was sieved, and polymer having a particle diameter (average particle diameter) of 300 μm to 600 μm was sieved to prepare superabsorbent polymer.

Experimental Example: Measurement of the Properties of the Superabsorbent Polymer Obtained in Examples and Comparative Examples For the superabsorbent polymer prepared in Examples and Comparative Examples, the properties were measured as follows, and the results are shown in Table 1 and Table 2.

Experimental Example 1. Centrifuge Retention Capacity (CRC) for a Saline Solution According to European Disposables and Nonwovens Association (EDANA) standard EDANA WSP 241.2, for the superabsorbent polymer of Examples and Comparative Examples, centrifuge retention capacity(CRC) by the absorption scale under no load was measured, and the results are described in the following Table 1.

That is, the polymer W(g) (about 0.2 g) respectively obtained through Examples and Comparative Examples was uniformly put in an envelope made of non-woven fabrics and sealed, which is then submerged into a saline solution made of 0.9 wt % sodium chloride aqueous solution at room temperature. After about 30 minutes elapsed, the envelope was drained for 3 minutes under 250 G condition using a centrifuge, and the weight of the envelope $W_2(g)$ was measured. And, after the same operation without using polymer, the weight at that time $W_1(g)$ was measured.

Using each obtained weight, CRC(g/g) was calculated according to the following Equation to confirm centrifuge retention capacity.

$$CRC(g/g) = \{[W_2(g) - W_1(g)]/W_0(g)\} - 1 \quad \text{[Equation 1]}$$

In the Equation 1, $W_0(g)$ is the initial weight of superabsorbent polymer(g), $W_1(g)$ is the weight of the apparatus measured after dehydration at 250 G for 3 minutes using a centrifuge, without using a superabsorbent polymer, and $W_2(g)$ is the weight of the apparatus including the superabsorbent polymer, measured after immersing the superabsorbent polymer in a 0.9 wt % saline solution for 30 minutes at room temperature to absorb, and then, dehydrating at 250 G for 3 minutes using a centrifuge.

Experimental Example 2. Extractable Content (EC)

According to EDANA method WSP 270.3, the extractable content of the superabsorbent polymer of Examples and Comparative Examples was measured, and the results are described in the following Table 1.

Experimental Example 3. Absorption Speed (Vortex-Test)

Into a 100 ml beaker, 50 ml of a 0.9 wt % NaCl solution was introduced, and then, each 2.00 g of the superabsorbent polymer according to Examples and Comparative Examples was added while stirring at 600 rpm using a stirrer. And, a time until the vortex of liquid generated by the stirring disappeared and a smooth surface was formed, was measured, and the results are described in the following Table 1.

TABLE 1

Compositions of superabsorbent polymers of Examples and Comparative Example and results of Experimental Examples

| | Cross linking agent (phr) | Inorganic particles (phr) | Blowing agent (phr) | Centrifuge retention capacity (g/g) | Extractable content (%) | Absorption speed (sec) |
|---|---|---|---|---|---|---|
| Example 1 | 0.23 | 0.18 | 1.0 | 46.4 | 21.7 | 53 |
| Example 2 | 0.15 | 0.18 | 1.0 | 52.1 | 26 | 57 |
| Comparative Example 1 | 0.23 | 0 | 0 | 47.1 | 21.7 | 65 |
| Comparative Example 2 | 0.23 | 0.18 | 0 | 49.0 | 21.7 | 61 |
| Comparative Example 3 | 0.34 | 0 | 0.3 | 40.6 | 18.7 | 75 |

*phr:weight ratio measured based on 100 parts by weight of ethylenically unsaturated monomers(acrylic acid)

As shown in Table 1, the superabsorbent polymers obtained in Examples 1 and 2 not only exhibit centrifuge retention capacity equivalent to that of the superabsorbent polymer obtained in Comparative Example 1 wherein inorganic particles and a blowing agent were not used, but also exhibit substantially decreased absorption speed of less than 60 seconds.

And, the superabsorbent polymer obtained in Comparative Example 2 wherein inorganic particles were used but a blowing agent was not used, and the superabsorbent polymer obtained in Comparative Example 3 wherein a blowing agent was used but inorganic particles were not used exhibit absorption speeds of 61 seconds and 75 seconds, respectively, and thus, it was confirmed that the superabsorbent polymers obtained in Examples 1 and 2 wherein inorganic particles and a blowing agent were used together has improved absorption speed of less than 60 seconds.

Thus, it was confirmed that the superabsorbent polymer of Examples wherein a blowing agent was added together with inorganic particles can realize remarkably improved absorption speed while maintaining optimum centrifuge retention capacity.

What is claimed is:

1. A superabsorbent polymer, comprising:
   a base resin powder comprising a crosslinked homopolymer of acrylic acid monomers having acid groups of which at least a part are neutralized,
   wherein a plurality of pores with a diameter of 1 μm or more are formed in the base resin powder,
   wherein the crosslinked homopolymer comprises layered silicate-based particles dispersed in a crosslinking structure,
   wherein the layered silicate-based particles comprise hectorite,
   wherein the superabsorbent polymer has a time for removing vortex generated of 60 seconds or less when stirring 2 grams of the superabsorbent polymer at 600 rpm in 50 ml of a 0.9 wt % NaCl solution, and
   wherein a centrifuge retention capacity for a saline solution, measured according to EDANA method WSP 241.2, is 45 g/g or more.

2. The superabsorbent polymer according to claim 1, wherein the plurality of pores with a diameter of 1 μm or more formed in the base resin powder comprise micropores with diameters of 10 μm to 100 μm.

3. The superabsorbent polymer according to claim 1, wherein the layered silicate-based particles comprise a unit crystal comprising a metal oxide layer, and a silica layer comprising silica formed on at least one side of the metal oxide layer.

4. The superabsorbent polymer according to claim 1, wherein the layered silicate-based particles have a column structure with a maximum diameter of a cross section of 1 nm to 100 nm, and a height of 0.1 nm to 20 nm.

5. The superabsorbent polymer according to claim 1, wherein the layered silicate-based particles are included in the content of 0.01 parts by weight to 5 parts by weight, based on 100 parts by weight of the base resin powder.

6. The superabsorbent polymer according to claim 1, wherein the crosslinked homopolymer comprises a crosslinking structure in which polymer chains of the acrylic acid monomers are crosslinked through crosslinkable functional groups of an internal crosslinking agent.

7. The superabsorbent polymer according to claim 1, wherein the crosslinked homopolymer comprises a crosslinked homopolymer formed by polymerization of the acrylic acid monomers in the presence of an internal crosslinking agent comprising a multifunctional acrylate-based compound.

8. The superabsorbent polymer according to claim 6, wherein the internal crosslinking agent comprises one or more selected from the group consisting of polyethyleneglycol diacrylate(PEGDA), glycerin diacrylate glycerin triacrylate, non-modified or ethoxylated trimethylol propane triacrylate(TMPTA), hexanedioldiacrylate, and triethyleneglycol diacrylate.

9. A method for preparing a superabsorbent polymer comprising steps of:
conducting a crosslinking polymerization of acrylic acid monomers having acid groups of which at least a part are neutralized, in the presence of layered silicate-based particles comprised hectorite, a blowing agent and an internal crosslinking agent, to form a hydrogel polymer; and
drying, grinding and sieving the hydrogel polymer to form a base resin powder, wherein the superabsorbent polymer comprises:
the base resin powder comprising a crosslinked homopolymer of the acrylic acid monomers having acid groups of which at least a part are neutralized,
wherein a plurality of pores with a diameter of 1 μm or more are formed in the base resin powder,
wherein the crosslinked homopolymer comprises the layered silicate-based particles dispersed in a crosslinking structure,
wherein the superabsorbent polymer has a time for removing vortex generated of 60 seconds or less when stirring 2 grams of the superabsorbent polymer at 600 rpm in 50 ml of a 0.9 wt % NaCl solution, and
wherein a centrifuge retention capacity for a saline solution, measured according to EDANA method WSP 241.2, is 45 g/g or more.

10. The method for preparing superabsorbent polymer according to claim 9, wherein, in the step of forming the hydrogel polymer, based on 100 parts by weight of the blowing agent, 1 to 1000 parts by weight of the layered silicate-based particles are used.

11. The method for preparing superabsorbent polymer according to claim 9, wherein the step of forming hydrogel polymer comprises steps of
forming a first solution comprising the internal crosslinking agent, and the acrylic acid monomers having acid groups of which at least a part are neutralized;
forming a second solution comprising the layered silicate-based particles and the blowing agent; and
progressing the crosslinking polymerization of a monomer composition comprising the first solution and the second solution.

12. The method for preparing superabsorbent polymer according to claim 11, wherein, in the step of forming the first solution comprising the internal crosslinking agent, and the acrylic acid monomers having acid groups of which at least a part are neutralized, the content of the internal crosslinking agent is 0.01 parts by weight to 5 parts by weight, based on 100 parts by weight of the acrylic acid monomers.

13. The method for preparing superabsorbent polymer according to claim 11, wherein, in the step of crosslinking polymerization of a monomer composition comprising the first solution and the second solution, the content of the second solution is 1 part by weight to 100 parts by weight, based on 100 parts by weight of the first solution included in the monomer composition.

14. The superabsorbent polymer according to claim 7, wherein the internal crosslinking agent comprises one or more selected from the group consisting of polyethyleneglycol diacrylate(PEGDA), glycerin diacrylate glycerin triacrylate, non-modified or ethoxylated trimethylol propane triacrylate(TMPTA), hexanedioldiacrylate, and triethyleneglycol diacrylate.

\* \* \* \* \*